(12) United States Patent
Liao (10) Patent No.: US 10,078,039 B2
(45) Date of Patent: Sep. 18, 2018

(54) INTEGRATED PROCESSING MECHANISM FOR UNIFORMLY-MIXING AND FILTERING SAMPLE

(71) Applicant: Qinghua Liao, Xiamen (CN)

(72) Inventor: Qinghua Liao, Xiamen (CN)

(73) Assignee: Qinghua LIAO, Xiamen, Fujian (CN)

( * ) Notice: Subject to any disclaimer, the term of this patent is extended or adjusted under 35 U.S.C. 154(b) by 66 days.

(21) Appl. No.: 15/313,069

(22) PCT Filed: Jan. 16, 2015

(86) PCT No.: PCT/CN2015/070830
§ 371 (c)(1),
(2) Date: Nov. 21, 2016

(87) PCT Pub. No.: WO2015/176548
PCT Pub. Date: Nov. 26, 2015

(65) Prior Publication Data
US 2017/0153168 A1    Jun. 1, 2017

(30) Foreign Application Priority Data
May 21, 2014   (CN) .................... 2014 2 0259808 U (51) Int. Cl.
*B01F 15/00* (2006.01)
*G01N 1/40* (2006.01)
(Continued)

(52) U.S. Cl.
CPC .......... *G01N 1/4077* (2013.01); *B01D 29/01* (2013.01); *B01D 36/001* (2013.01); *B01F 9/00* (2013.01);
(Continued)

(58) Field of Classification Search
CPC .............. B01F 7/00008; B01F 7/00433; B01F 15/00772; B01F 1/007985
See application file for complete search history.

(56) References Cited

U.S. PATENT DOCUMENTS 4,172,524 A * 10/1979 Holm .................... B07C 5/3408
209/524
4,186,542 A * 2/1980 Oyagi ...................... B67B 1/04
53/109
(Continued)

FOREIGN PATENT DOCUMENTS

CN           1963527 A       5/2007
CN         101874946 A      11/2010
(Continued)

OTHER PUBLICATIONS

International Search Report dated Apr. 15, 2015 for the corresponding PCT Application No. PCT/CN2015/070830.

*Primary Examiner* — David A Rogers
(74) *Attorney, Agent, or Firm* — Leason Ellis LLP (57) ABSTRACT

A filtering and ventilating mechanism is driven by motors. The filtering mechanism rotates and presses downwards so its pressing surface is against a sample container. A ventilation needle is inserted into the sample container for ventilation. A mixing mechanism is arranged below the filtering mechanism and is driven by a mixing motor. The sample container is accommodated in a seat and is driven by the mixing motor. A test tube carrying mechanism is arranged below the mixing mechanism, and has an accommodating hole for a test tube. A jacking mechanism is arranged below the mixing mechanism, and is driven by a jacking motor. When the jacking mechanism moves upwards, a jacking platform is pressed against the bottom of the test tube, so that the test tube is butted against the bottom
(Continued)

of the sample container, and a sample preparation in the sample container is dripped into the test tube.

7 Claims, 7 Drawing Sheets

(51) Int. Cl.
*B01F 9/00* (2006.01)
*B01D 29/01* (2006.01)
*B01D 36/00* (2006.01)
*B01F 9/20* (2006.01)
*G01N 1/38* (2006.01)

(52) U.S. Cl.
CPC ............... *B01F 9/002* (2013.01); *B01F 9/20* (2013.01); *G01N 1/38* (2013.01); *B01F 15/00772* (2013.01); *B01F 2215/0037* (2013.01); *G01N 2001/4088* (2013.01)

(56) References Cited

U.S. PATENT DOCUMENTS

| | | | | |
|---|---|---|---|---|
| 4,271,123 A * | 6/1981 | Curry | ................ | B01L 9/06 422/64 |
| 4,305,668 A * | 12/1981 | Bilbrey | ................ | B01F 11/00 366/111 |
| 5,171,531 A | 12/1992 | Chiristianson et al. | | |
| 5,215,376 A * | 6/1993 | Schulte | ................ | B01F 11/0002 141/265 |
| 5,318,359 A * | 6/1994 | Wakatake | ................ | B01L 9/06 366/140 |
| 5,439,645 A * | 8/1995 | Saralegui | ................ | B01F 11/0014 366/128 |
| 5,819,508 A * | 10/1998 | Kraft | ................ | B67B 7/02 53/492 |
| 6,103,193 A * | 8/2000 | Iwahashi | ................ | G01N 33/5302 422/236 |
| 6,393,900 B1 * | 5/2002 | Buckner, III | ................ | G01N 1/04 141/51 |
| 6,461,034 B1 * | 10/2002 | Cleveland | ................ | B01F 7/00291 366/273 |
| 6,500,343 B2 * | 12/2002 | Siddiqi | ................ | B03C 1/01 210/695 |
| 6,544,799 B1 * | 4/2003 | Lewis | ................ | G01N 30/24 422/63 |
| 7,165,734 B2 * | 1/2007 | Bucher | ................ | B01F 7/00008 241/199.12 |
| 7,985,375 B2 * | 7/2011 | Edens | ................ | G01N 35/0099 422/50 |
| 8,286,671 B1 * | 10/2012 | Strangis | ................ | B65B 7/28 141/104 |
| 8,444,130 B2 * | 5/2013 | Sink | ................ | G07F 11/70 269/56 |
| 8,596,566 B2 * | 12/2013 | Hsu | ................ | B02C 17/10 241/174 |
| 8,807,177 B2 * | 8/2014 | Strangis | ................ | B63C 9/0005 141/104 |
| 9,400,285 B2 * | 7/2016 | Ochranek | ................ | G01N 35/025 |
| 2003/0092186 A1 * | 5/2003 | Pressman | ................ | B01D 61/18 436/46 |
| 2004/0252582 A1 * | 12/2004 | Bucher | ................ | B01F 7/00008 366/273 |
| 2007/0222973 A1 * | 9/2007 | Hoshiko | ................ | G01N 21/253 356/39 |
| 2008/0044311 A1 * | 2/2008 | Iguchi | ................ | G01N 35/1009 422/63 |
| 2008/0134537 A1 * | 6/2008 | Damen | ................ | F26B 5/06 34/92 |
| 2008/0247914 A1 * | 10/2008 | Edens | ................ | G01N 35/0099 422/400 |
| 2008/0311678 A1 * | 12/2008 | Ootani | ................ | G01N 35/0098 436/526 |
| 2009/0004681 A1 * | 1/2009 | Hoshiko | ................ | G01N 33/4905 435/13 |
| 2009/0028754 A1 * | 1/2009 | Robb | ................ | B01L 9/06 422/65 |
| 2009/0178370 A1 * | 7/2009 | Uebel | ................ | B67B 3/264 53/314 |
| 2011/0100501 A1 * | 5/2011 | Mizuno | ................ | A61J 3/002 141/2 |
| 2012/0241042 A1 * | 9/2012 | Strangis | ................ | B65B 7/28 141/2 |
| 2012/0325365 A1 * | 12/2012 | Strangis | ................ | B63C 9/0005 141/2 |
| 2012/0325368 A1 * | 12/2012 | Strangis | ................ | B63C 9/0005 141/18 |
| 2014/0178269 A1 * | 6/2014 | Zilberberg | ................ | B01L 9/06 422/562 |
| 2017/0136465 A1 * | 5/2017 | Pohl | ................ | B01L 3/5635 |

FOREIGN PATENT DOCUMENTS

| | | | | |
|---|---|---|---|---|
| CN | 103990403 A | 8/2014 | | |
| CN | 203862180 U | 10/2014 | | |
| CN | 104502178 A | * 4/2015 | ............... | G01N 1/38 |
| CN | 204816359 U | * 12/2015 | ............... | B01F 11/00 |

* cited by examiner

INTEGRATED PROCESSING MECHANISM FOR UNIFORMLY-MIXING AND FILTERING SAMPLE

CROSS-REFERENCE TO RELATED PATENT APPLICATIONS

This application is a U.S. National Phase Application under 35 U.S.C. § 371 of International Patent Application No. PCT/CN2015/070830, filed Jan. 16, 2015 and claims priority from Chinese Application No. 201420259808.7, filed May 21, 2014, which are incorporated herein by reference in their entireties. The International Application was published in Chinese on Nov. 26, 2015 as International Publication No. WO/2015/176548 A1.

FIELD OF THE INVENTION

The present application relates to a mechanism for uniformly-mixing and filtering sample preparations, and specifically relates to an integrated processing mechanism for uniformly-mixing and filtering samples.

BACKGROUND OF THE INVENTION

In the laboratory field and the industrial field, solutions or solid matters need to be dissolved, uniformly-mixed, and then filtered to remove large particle matters. A common method is manually operating or pumping liquid from a container into a filtering device.

Figure 9:
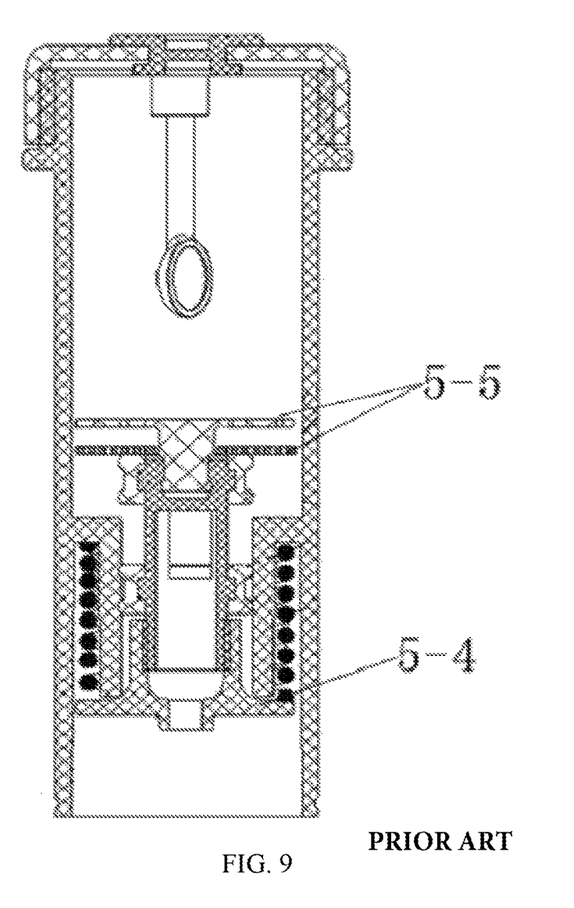
FIG. 9 is a schematic view of a sample container with a filtering function.

At present, there have already been containers with filtering devices on the market, for example, the invention patent with the application number 200910140542.8 describes a sample container 5 with a structure as shown in FIG. 9. An inner bottom of the sample container is provided with a filtering mesh, and when a filtering hole at a bottom of the sample container is opened, liquid in the container flows downwards, passes through the filtering mesh at the bottom of the container, and drips into a test tube.

This technology can also realize filtering by manual operations, but it consumes much time and work, and is prone to cause situations of incomplete filtering and inability to cooperate with an automatic equipment.

SUMMARY OF THE INVENTION

Aiming at the defects existing in the prior art, the present application provides an integrated processing mechanism for uniformly-mixing and filtering samples, such that uniformly-mixing and filtering functions of a sample container can be realized automatically.

In order to realize the aforesaid purpose, the present application provides the following technical solution.

An integrated processing mechanism for uniformly-mixing and filtering samples comprises a filtering and ventilating mechanism, a test tube, a uniformly-mixing mechanism, a test tube carrying mechanism, a sample container, and a jacking mechanism cooperating sequentially; wherein, the filtering and ventilating mechanism is driven by motors to move vertically and rotate horizontally, and the filtering and ventilating mechanism has a pressing surface and a ventilation needle; when the filtering and ventilating mechanism rotates and moves downwards, the pressing surface presses the sample container, and the ventilation needle is inserted into the sample container for ventilation; the uniformly-mixing mechanism is arranged below the filtering and ventilating mechanism and driven by a uniformly-mixing motor to rotate forwardly and reversely; the uniformly-mixing mechanism has a hollow uniformly-mixing base, and the sample container is accommodated in the hollow uniformly-mixing base and driven by the uniformly-mixing motor to rotate forwardly and reversely; the test tube carrying mechanism is arranged below the uniformly-mixing mechanism and has an accommodating hole configured to receive the test tube; the jacking mechanism is arranged below the uniformly-mixing mechanism and driven by a jacking motor to move vertically; the jacking mechanism includes a jacking platform, and when the jacking mechanism moves upwards, the jacking platform is pressed against a bottom of the test tube so as to ensure that the test tube is butted with a bottom of the sample container, such that sample preparation in the sample container drips into the test tube.

Furthermore, the filtering and ventilating mechanism includes the ventilation needle, an upper cover, a spring, a hollow main body base, a rebounding mechanism, a left-right swing motor, an up-down moving motor, and the pressing surface; wherein, the upper cover is fixed on the hollow main body base; at a lower portion of the hollow main body base, the pressing surface and an outer wall form a receiving cavity, the pressing surface is provided with an opening, the ventilation needle is fixed on the upper cover, and a tail end of the ventilation needle extends into the receiving cavity; the rebounding mechanism is arranged in the hollow main body base and movably sheathed outside the upper cover and the ventilation needle, a bottom part of the rebounding mechanism extends out of the opening, and the bottom part of the rebounding mechanism is provided with a hole allowing the ventilation needle to extend out; the spring is sheathed outside rebounding mechanism and compressed between the rebounding mechanism and the upper cover.

Furthermore, the uniformly-mixing mechanism includes a uniformly-mixing base, which is a hollow structure and enables the test tube to pass through a hollow uniformly-fixing area; the uniformly-fixing base is driven by a uniformly-fixing driving mechanism to rotate forwardly and reversely.

Furthermore, the test tube carrying mechanism includes one or a plurality of hole site(s) configured to position one or a plurality of test tube(s), and the test tube(s) move(s) to a location below a bottom of the uniformly-mixing base when being driven manually or by a carrying mechanism motor.

Furthermore, a supporting block is arranged between the ventilation needle and the upper cover.

Furthermore, the uniformly-mixing driving mechanism includes a uniformly-mixing motor base, and the uniformly-mixing motor is fixed on the uniformly-mixing motor base; the uniformly-mixing motor (3-7) drives a first synchronous wheel to rotate, the first synchronous wheel drives a second synchronous wheel to rotate via a first belt, the uniformly-mixing base is fixed to and rotates along with the second synchronous wheel, an upper pressing base is sheathed outside an upper portion of the uniformly-mixing base, bearings are disposed between the uniformly-mixing base and the upper pressing base and between the uniformly-mixing base and the uniformly-mixing motor base, and a gasket is disposed between the uniformly-mixing base and an upper bearing.

Furthermore, the test tube carrying mechanism includes a carrying base, and a carrying mechanism motor is fixed on the carrying base; the carrying mechanism motor drives a third synchronous wheel to rotate, the third synchronous wheel drives a fourth synchronous wheel to rotate via a second belt, a rotating wheel is fixed to and rotates along with the fourth synchronous wheel, and the rotating wheel is provide with one or a plurality of hole sites configured to carrying the suspension-type test tubes.

By adopting the aforementioned technical solutions, the present application has the following advantages:

1. The structure is simple, and the uniformly-mixing function and the filtering function are integrated.

2. The ventilation needle of the filtering and ventilating mechanism communicates the inner space of the sample container 5 with the external space, and thus avoids the situation that a negative pressure is generated inside the sample container and filtering is unable to be completed. The filtering and ventilating mechanism has the rebounding mechanism, which prevents the sample container from being separated from the uniformly-mixing base.

3. The rotating wheel for positioning the suspension-type test tubes can be designed to have one position or have a plurality of positions, such that the requirement for continuously filtering is met.

DETAILED DESCRIPTION OF THE PREFERRED EMBODIMENT

The present application is further described below with reference to the accompany drawings and embodiments.

As shown in FIGS. 1-9, an embodiment of the present application provides an integrated processing mechanism for uniformly-mixing and filtering samples, which comprises a filtering and ventilating mechanism 1, a test tube 2, a uniformly-mixing mechanism 3, a test tube carrying mechanism 4, a sample container 5, and a jacking mechanism 6 cooperating sequentially; wherein, the filtering and ventilating mechanism 1 is driven by motors to move vertically and rotate horizontally, and the filtering and ventilating mechanism 1 has a pressing surface 1-9 and a ventilation needle 1-1; when the filtering and ventilating mechanism 1 rotates and moves downwards, the pressing surface 1-9 presses the sample container 5, and the ventilation needle 1-1 is inserted into the sample container 1 for ventilation; the uniformly-mixing mechanism 3 is arranged below the filtering and ventilating mechanism 1 and driven by a uniformly-mixing motor 3-7 to rotate forwardly and reversely; the uniformly-mixing mechanism 3 has a hollow uniformly-mixing base 3-4, and the sample container 5 is accommodated in the hollow uniformly-mixing base 3-4 and driven by a uniformly-mixing motor 3-7 to rotate forwardly and reversely; the test tube carrying mechanism 4 is arranged below the uniformly-mixing mechanism 3 and has an accommodating hole configured to receive the test tube 2; the jacking mechanism 6 is arranged below the uniformly-mixing mechanism 3 and driven by a jacking motor 6-2 to move vertically; the jacking mechanism 6 includes a jacking platform 6-1, and when the jacking mechanism 6 moves upwards, the jacking platform 6-1 is pressed against a bottom of the test tube 2 so as to ensure that the test tube 2 is butted with a bottom of the sample container 5, such that sample preparation in the sample container 5 drips into the test tube 2.

In the present application, by continuous actions of the aforesaid mechanisms, the sample preparation in the sample container 5 is uniformly-mixed and dripped into the test tube 2 to be operated by the next procedure.

Figure 1:
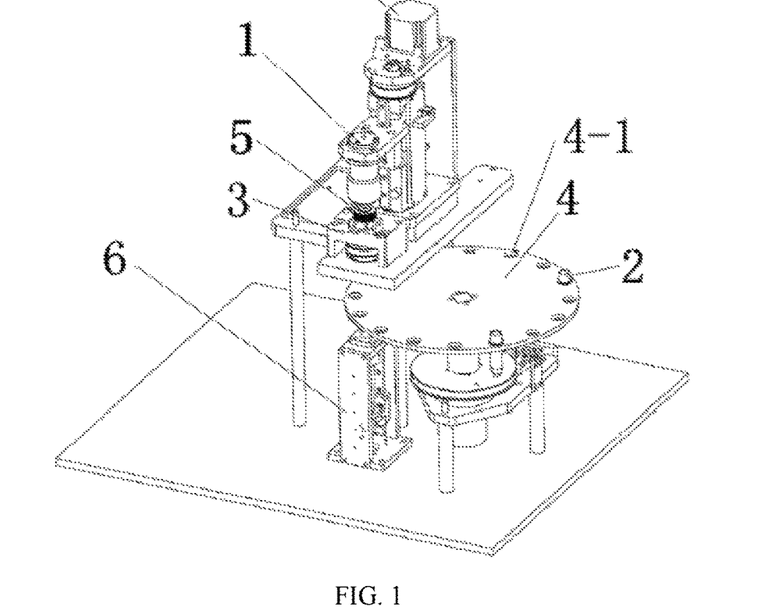
FIG. 1 is a whole schematic view of a uniformly-mixing and filtering mechanism.
Figure 2:
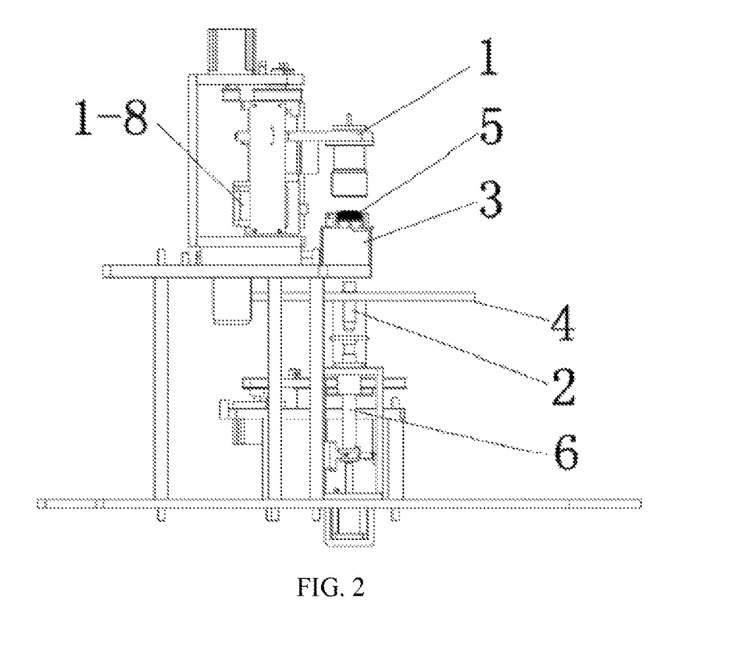
FIG. 2 is a plan schematic view of the whole uniformly-mixing and filtering mechanism.
Figure 3:
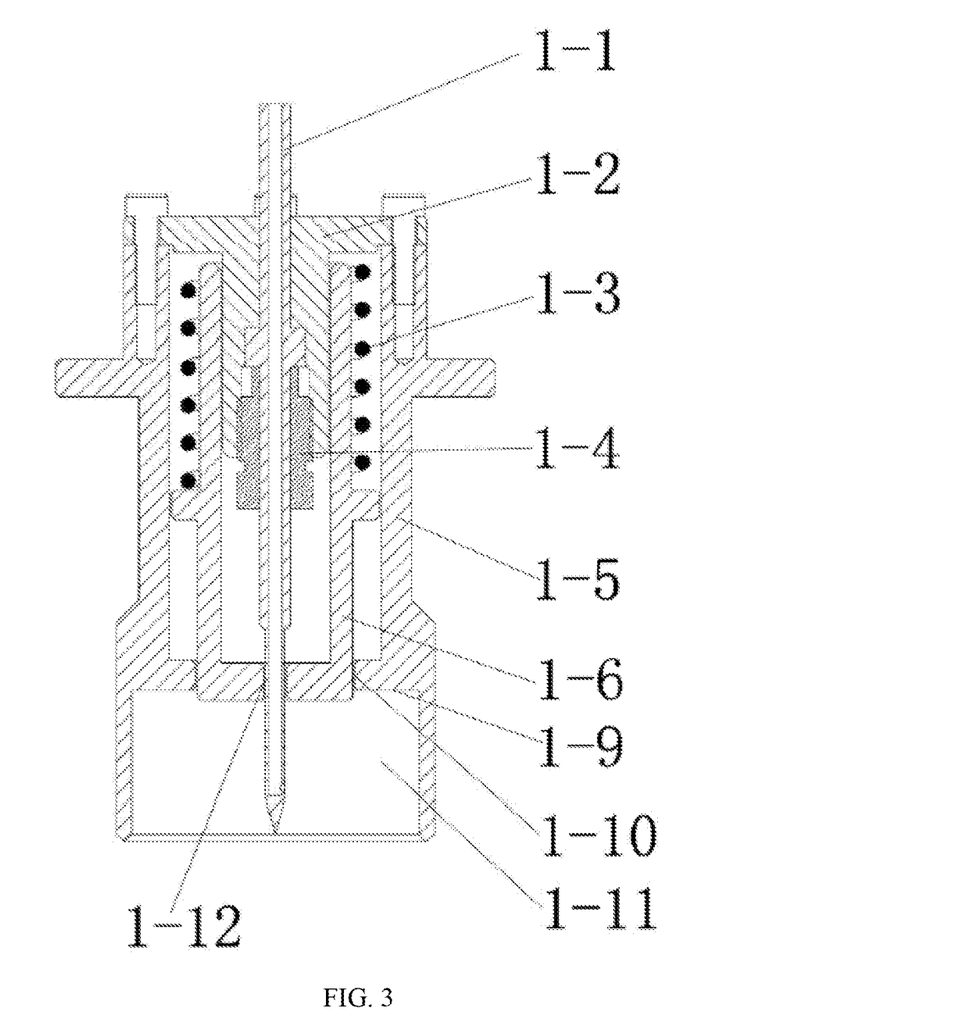
FIG. 3 is a schematic view of a filtering and ventilating mechanism.

In actual use, the aforesaid filtering and ventilating mechanism 1 can specifically adopt the structure as shown in FIG. 3, which comprises the ventilation needle 1-1, an upper cover 1-2, a spring 1-3, a hollow main body base 1-5, a rebounding mechanism 1-6, a left-right swing motor 1-7, an up-down moving motor 1-8, and the pressing surface 1-9; wherein, the upper cover 1-2 is fixed on the hollow main body base 1-5; at a lower portion of the hollow main body base 1-5, the pressing surface 1-9 and an outer wall form a receiving cavity 1-10; the pressing surface 1-9 is provided with an opening 1-11, the ventilation needle 1-1 is fixed on the upper cover 1-2, and a tail end of the ventilation needle 1-1 extends into the receiving cavity 1-10; the rebounding mechanism 1-6 is arranged in the hollow main body base 1-5 and movably sheathed outside the upper cover 1-2 and the ventilation needle 1-1, a bottom part of the rebounding mechanism 1-6 extends out of the opening 1-11, and the bottom part of the rebounding mechanism 1-6 is provided with a hole 1-12 allowing the ventilation needle 1-1 to extends out; the spring 1-3 is sheathed outside rebounding mechanism 1-6 and compressed between the rebounding mechanism 1-6 and the upper cover 1-2; and a supporting block 1-4 is disposed between the ventilation needle 1-1 and the upper cover 1-2.

Figure 4:
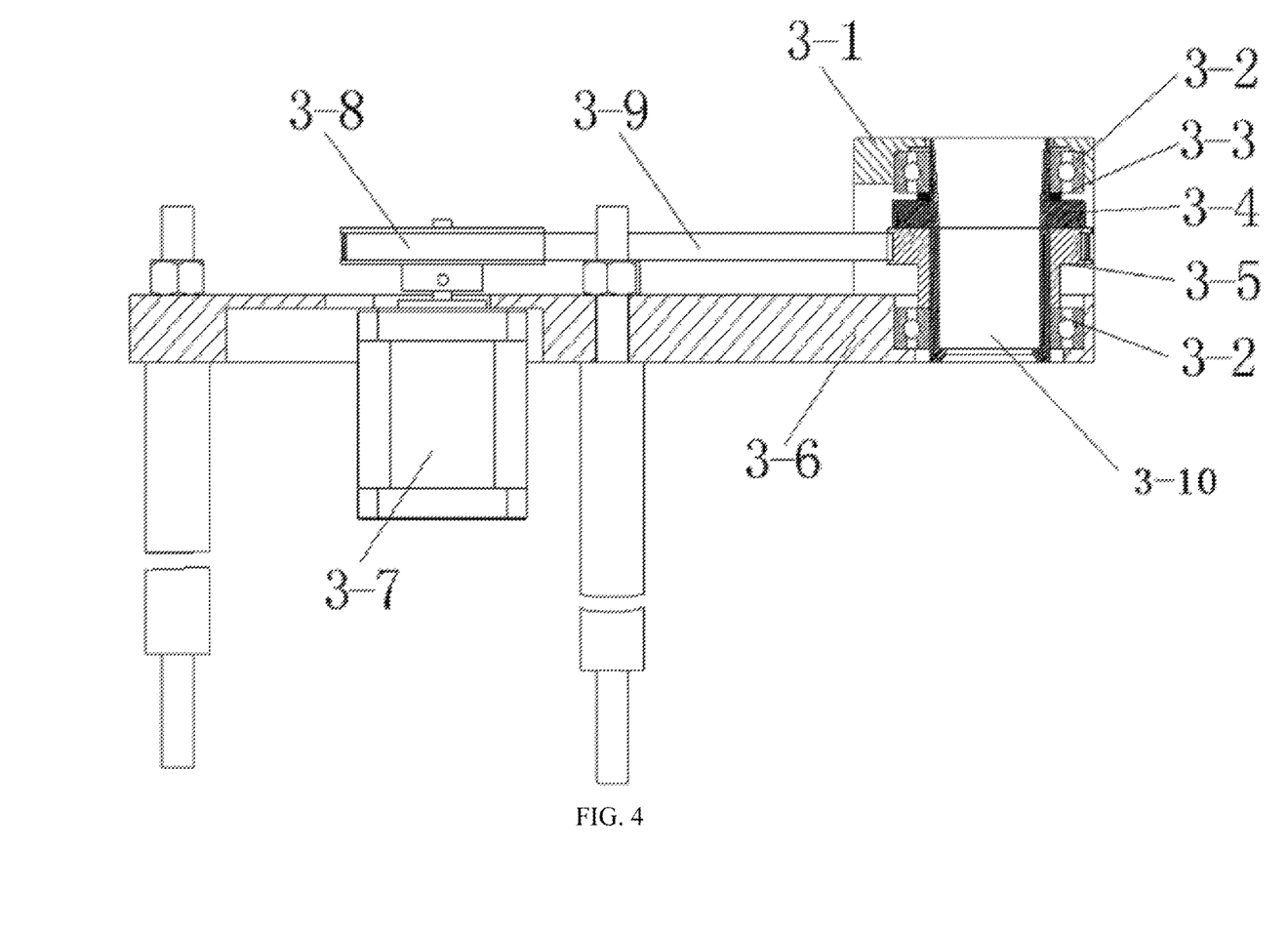
FIG. 4 is a schematic view of a uniformly-mixing mechanism.

The uniformly-mixing mechanism 3 can adopt the specific structure as shown in FIG. 4: the uniformly-mixing driving mechanism includes a uniformly-mixing motor base 3-6, and the uniformly-mixing motor 3-7 is fixed on the uniformly-mixing motor base 3-6; the uniformly-mixing motor 3-7 drives a first synchronous wheel 3-8 to rotate, the first synchronous wheel 3-8 drives a second synchronous wheel 3-5 to rotate via a first belt 3-9, the uniformly-mixing base 3-4 is fixed to and rotates along with the second synchronous wheel 3-5, an upper pressing base 3-1 is sheathed outside an upper portion of the uniformly-mixing base 3-4, bearings 3-2 are disposed between the uniformly-mixing base 3-4 and the upper pressing base 3-1 and between the uniformly-mixing base 3-4 and the uniformly-mixing motor base 3-6, and a gasket 3-3 is disposed between the uniformly-mixing base 3-4 and an upper bearing.

Figure 7:
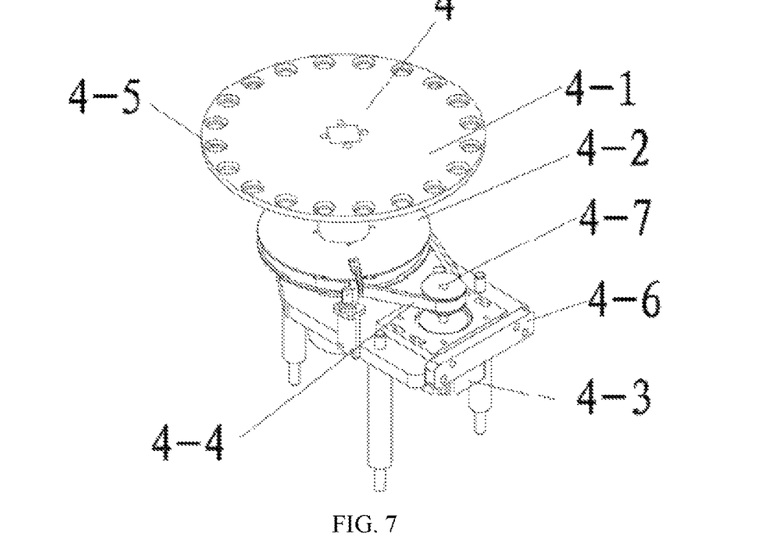
FIG. 7 is a schematic view of a test tube rotating wheel mechanism.
Figure 8:
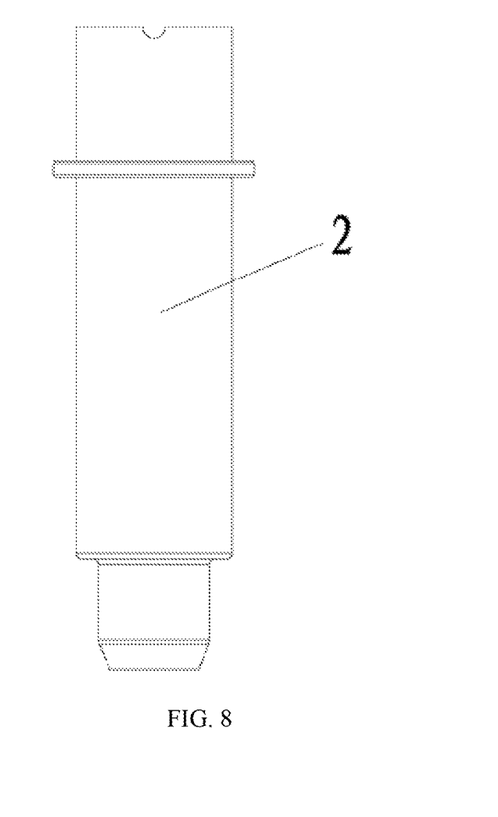
FIG. 8 is a schematic view of a suspension-type test tube.

The test tube carrying mechanism 4 can have a specific structure as shown in FIG. 7, which has one or a plurality of hole site(s) configured to position one or a plurality of test tube(s) 2, and the test tube(s) 2 move(s) to a location below a bottom of the uniformly-mixing base 3-4 when being driven manually or by a carrying mechanism motor 4-3; wherein, the carrying mechanism motor 4-3 is fixed on a carrying base 4-6; the carrying mechanism motor 4-3 drives a third synchronous wheel 4-7 to rotate, the third synchronous wheel 4-7 drives a fourth synchronous wheel 4-2 to rotate via a second belt 4-4, a rotating wheel 4-1 is fixed to and rotates along with the fourth synchronous wheel 4-7, and the rotating wheel 4-1 is provide with one or a plurality of hole sites configured to carrying the suspension-type test tubes 2. A specific structure of each suspension-type test tube 2 can be a structure disclosed by the patent with the application number 201320231856.0.

A working process of the present application is described below according to the specific structures disclosed by the embodiment shown in FIGS. 1-9. In use, a suspension-type test tube 2 is positioned on a test tube carrying rotating wheel 4-5, the carrying mechanism motor 4-3 is started and drives the rotating wheel to move the test tube to a location that is below the uniformly-mixing base 3-4 in a vertical direction. The sample container 5 is placed into the uniformly-mixing base 3-4, the uniformly-mixing motor rotates forwardly and reversely, and then drives the uniformly-mixing base 3-4 and the sample container 5 therein to rotate forwardly and reversely too. Liquid in the sample container 5 is uniformly-mixed during the forwardly and reversely rotating uniformly-mixing processes. When uniformly-mixing is completed, the uniformly-mixing motor stops, the filtering and ventilating mechanism 1 moves downwards, the pressing surface is pressed against the sample container 5; at this time, the filtering ventilation needle 1-1 enters the sample container 5, such that the pressure inside the sample container 5 is communicated with an external pressure and thus a negative pressure inside the container is prevented from being generated. The rebounding mechanism 1-6 is pressed, and the spring 1-3 is compressed. The filtering jacking mechanism 6-1 moves upwards, so as to push the suspension-type test tube 2 to move upwards and further make a filtering device 5-4 at a bottom of the sample container 5 move upwards; the filtering hole is opened, and the liquid in the sample container 5 passes through an inner filtering mesh 5-5 and flows downwards into the suspension-type test tube 2.

Figure 5:
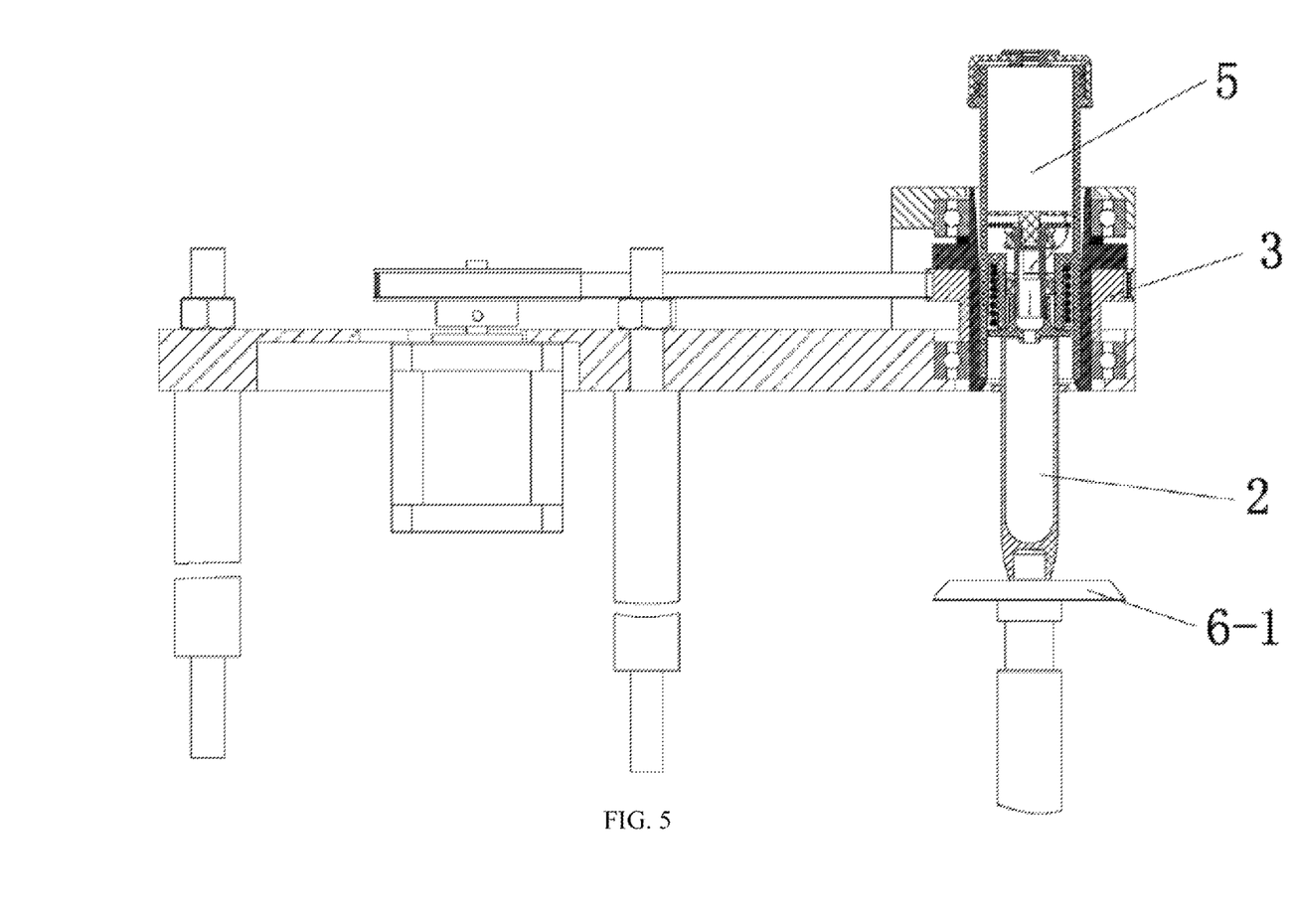
FIG. 5 is a schematic view of a filtering operation.
Figure 6:
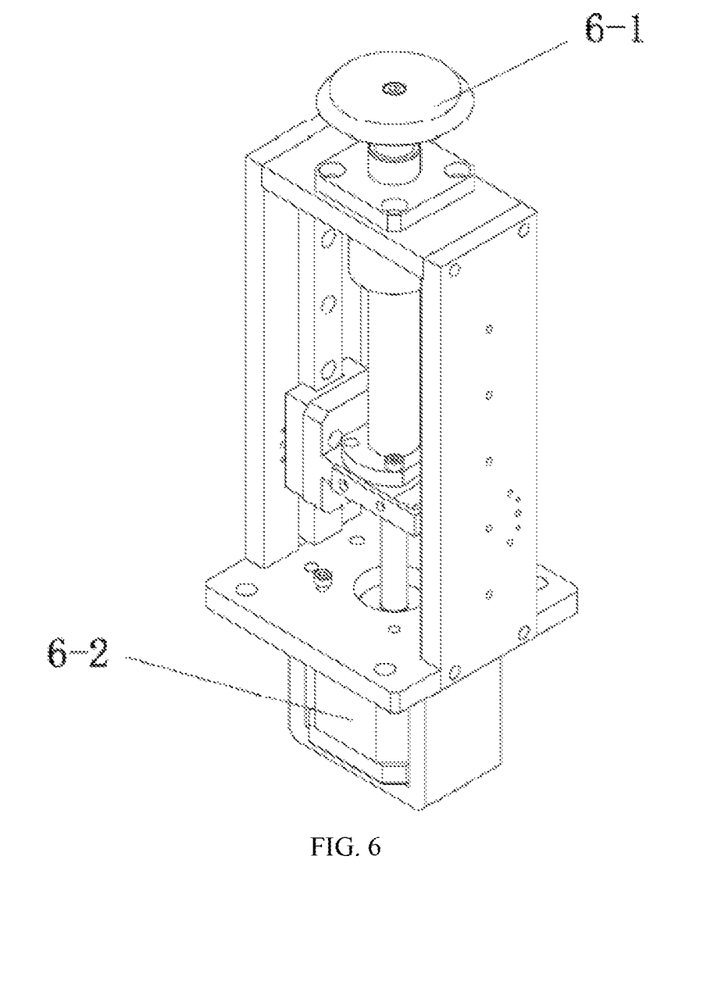
FIG. 6 is a schematic view of a filtering jacking mechanism.

When filtering is completed, the filtering jacking mechanism 6-1 moves downwards to return its original location, and the suspension-type test tube 2 synchronously moves downwards to be separated from the sample container 5 and hung on the rotating wheel 4. The filtering and ventilating mechanism 1 moves upwards, and the rebounding mechanism 1-6 moves downwards under the counterforce of the spring 1-3, such that the sample container 5 is separated from the filtering ventilation needle 101, thereby avoiding the sample container 5 from being separated from the uniformly-mixing base. Thus, the whole uniformly-mixing and filtering operation is completed.

The present application is simple in structure, and integrates a uniformly-mixing function and a filtering function. The ventilation needle of the filtering and ventilating mechanism communicates the inner space of the sample container with the external space, and thus avoids the situation that a negative pressure is generated inside the sample container and filtering is unable to be completed. The filtering and ventilating mechanism has the rebounding mechanism, which prevents the sample container from being separated from the uniformly-mixing base. The rotating wheel for positioning the suspension-type test tubes can be designed to have one position or have a plurality of positions, such that the requirement for continuously filtering is met.

The above description illustrates and describes an preferred embodiment of the present invention. As detailed above, it should be understood that the present application is not limited by the manner disclosed by this disclosure and should not be regarded as eliminating other embodiments, but can be used in other various combinations, modifications, and environments. Moreover, the present application can be modified according to the aforesaid instruction or technology or knowledge in related fields within the invention conception scope of this disclosure. Any modification and change made by one of ordinary skill in the art should be included in the protection scopes of the accompanying claims of the present application if they do not depart from the spirit and scope of the present application.

What is claimed is:

1. An integrated processing mechanism for uniformly-mixing and filtering samples comprising a filtering and ventilating mechanism (1), a test tube (2), a uniformly-mixing mechanism (3), a test tube carrying mechanism (4), a sample container (5), and a jacking mechanism (6) cooperating sequentially; wherein, the filtering and ventilating mechanism (1) is driven by motors to move vertically and rotate horizontally, and the filtering and ventilating mechanism (1) has a pressing surface (1-9) and a ventilation needle (1-1); when the filtering and ventilating mechanism (1) rotates and moves downwards, the pressing surface (1-9) presses the sample container (5), and the ventilation needle (1-1) is inserted into the sample container (5) for ventilation; the uniformly-mixing mechanism (3) is arranged below the filtering and ventilating mechanism (1) and driven by a uniformly-mixing motor (3-7) to rotate forwardly and reversely; the uniformly-mixing mechanism (3) has a hollow uniformly-mixing base (3-4), and the sample container (5) is accommodated in the hollow uniformly-mixing base (3-4) and driven by the uniformly-mixing motor (3-7) to rotate forwardly and reversely; the test tube carrying mechanism (4) is arranged below the uniformly-mixing mechanism (3) and has an accommodating hole configured to receive the test tube (2); the jacking mechanism (6) is arranged below the uniformly-mixing mechanism (3) and driven by a jacking motor (6-2) to move vertically; the jacking mechanism (6) includes a jacking platform (6-1), and when the jacking mechanism (6) moves upwards, the jacking platform (6-1) is pressed against a bottom of the test tube (2) so as to ensure that the test tube (2) is butted with a bottom of the sample container (5), such that sample preparation in the sample container (5) drips into the test tube (2).

2. The integrated processing mechanism for uniformly-mixing and filtering samples according to claim 1, wherein, the filtering and ventilating mechanism (1) includes the ventilation needle (1-1), an upper cover (1-2), a spring (1-3), a hollow main body base (1-5), a rebounding mechanism (1-6), a left-right swing motor (1-7), an up-down moving motor (1-8), and the pressing surface (1-9); wherein, the upper cover (1-2) is fixed on the hollow main body base (1-5); at a lower portion of the hollow main body base (1-5), the pressing surface (1-9) and an outer wall form a receiving cavity (1-10), the pressing surface (1-9) is provided with an opening (1-11), the ventilation needle (1-1) is fixed on the upper cover (1-2), and a tail end of the ventilation needle (1-1) extends into the receiving cavity (1-10); the rebounding mechanism (1-6) is arranged in the hollow main body base (1-5) and movably sheathed outside the upper cover (1-2) and the ventilation needle (1-1), a bottom part of the rebounding mechanism (1-6) extends out of the opening (1-11), and the bottom part of the rebounding mechanism (1-6) is provided with a hole (1-12) allowing the ventilation needle (1-1) to extend out; the spring (1-3) is sheathed outside rebounding mechanism (1-6) and compressed between the rebounding mechanism (1-6) and the upper cover (1-2).

3. The integrated processing mechanism for uniformly-mixing and filtering samples according to claim 1, wherein, the uniformly-mixing mechanism (3) includes a uniformly-mixing base (3-4), which is a hollow structure and enables the test tube (2) to pass through a hollow uniformly-fixing area; the uniformly-fixing base (3-4) is driven by a uniformly-fixing driving mechanism to rotate forwardly and reversely.

4. The integrated processing mechanism for uniformly-mixing and filtering samples according to claim 1, wherein, the test tube carrying mechanism (4) includes one or a plurality of hole site(s) configured to position one or a plurality of test tube(s) (2), and the test tube(s) (2) move(s) to a location below a bottom of the uniformly-mixing base (3-4) when being driven manually or by a carrying mechanism motor (4-3).

5. The integrated processing mechanism for uniformly-mixing and filtering samples according to claim 2, wherein, a supporting block (1-4) is arranged between the ventilation needle (1-1) and the upper cover (1-2).

6. The integrated processing mechanism for uniformly-mixing and filtering samples according to claim 3, wherein, the uniformly-mixing driving mechanism includes a uniformly-mixing motor base (3-6), and the uniformly-mixing motor (3-7) is fixed on the uniformly-mixing motor base (3-6); the uniformly-mixing motor (3-7) drives a first synchronous wheel (3-8) to rotate, the first synchronous wheel (3-8) drives a second synchronous wheel (3-5) to rotate via a first belt (3-9), the uniformly-mixing base (3-4) is fixed to and rotates along with the second synchronous wheel (3-5), an upper pressing base (3-1) is sheathed outside an upper portion of the uniformly-mixing base (3-4), bearings (3-2) are disposed between the uniformly-mixing base (3-4) and the upper pressing base (3-1) and between the uniformly-mixing base (3-4) and the uniformly-mixing motor base (3-6), and a gasket (3-3) is disposed between the uniformly-mixing base (3-4) and an upper bearing.

7. The integrated processing mechanism for uniformly-mixing and filtering samples according to claim 4, wherein, the test tube carrying mechanism (4) includes a carrying base (4-6), and a carrying mechanism motor (4-3) is fixed on the carrying base (4-6); the carrying mechanism motor (4-3) drives a third synchronous wheel (4-7) to rotate, the third synchronous wheel (4-7) drives a fourth synchronous wheel (4-2) to rotate via a second belt (4-4), a rotating wheel (4-1) is fixed to and rotates along with the fourth synchronous wheel (4-7), and the rotating wheel (4-1) is provide with one or a plurality of hole sites configured to carrying the suspension-type test tubes (2).

\* \* \* \* \*